(12) United States Patent
Zhao

(10) Patent No.: US 12,072,751 B2
(45) Date of Patent: Aug. 27, 2024

(54) WEARING STATE DETECTION METHOD, WEARING STATE DETECTION DEVICE AND WEARABLE DEVICE

(71) Applicant: SHENZHEN GOODIX TECHNOLOGY CO., LTD., Shenzhen (CN)

(72) Inventor: Wanruonan Zhao, Shenzhen (CN)

(73) Assignee: SHENZHEN GOODIX TECHNOLOGY CO., LTD., Shenzhen (CN)

(*) Notice: Subject to any disclaimer, the term of this patent is extended or adjusted under 35 U.S.C. 154(b) by 20 days.

(21) Appl. No.: 17/744,532

(22) Filed: May 13, 2022

(65) Prior Publication Data

US 2022/0283623 A1 Sep. 8, 2022

Related U.S. Application Data

(63) Continuation of application No. PCT/CN2020/126071, filed on Nov. 3, 2020.

(51) Int. Cl.
*G06F 1/3231* (2019.01)
*G06F 1/16* (2006.01)
(Continued)

(52) U.S. Cl.
CPC ............ *G06F 1/3231* (2013.01); *G06F 1/163* (2013.01); *G06F 3/011* (2013.01); *G06F 3/0304* (2013.01)

(58) Field of Classification Search
CPC ....... G06F 1/163; G06F 1/3231; G06F 3/0304
See application file for complete search history.

(56) References Cited

U.S. PATENT DOCUMENTS

2016/0341600 A1* 11/2016 Aloe .................... G01V 8/12
2017/0215747 A1* 8/2017 van Dinther ......... A61B 5/6826
(Continued)

FOREIGN PATENT DOCUMENTS

CN 105592780 A 5/2016
CN 106153098 A 11/2016
(Continued)

OTHER PUBLICATIONS

Search Report in International Application No. PCT/CN2020/126071 dated Nov. 3, 2020, 5 pages (No English Translation).
(Continued)

*Primary Examiner* — Matthew A Eason
*Assistant Examiner* — Chayce R Bibbee
(74) *Attorney, Agent, or Firm* — Suiter Swantz IP

(57) ABSTRACT

A wearing state detection method, a wearing state detection device, and a wearable device are provided. The method detects a wearing state of the wearable device and includes: emitting, by the light emitting unit, light of at least two different wavelengths to a subject in a time division manner; receiving, by the light receiving unit, reflected light corresponding to light of each wavelength after being reflected by the subject; obtaining intensity of reflected light corresponding to the light of each wavelength respectively; calculating a fluctuation range of a light intensity ratio, which is a ratio between intensity of the reflected light corresponding to light of the at least two different wavelengths received by a same light receiving unit; and determining that the device is in a wearing state when the fluctuation range is greater than or equal to a first threshold.

17 Claims, 8 Drawing Sheets

(51) Int. Cl.
G06F 3/01      (2006.01)
G06F 3/03      (2006.01)

(56) References Cited

U.S. PATENT DOCUMENTS

| | | |
|---|---|---|
| 2019/0069781 A1 | 3/2019 | Kim et al. |
| 2019/0274628 A1* | 9/2019 | Duan .................... A61B 5/681 |
| 2020/0146629 A1* | 5/2020 | Sun ...................... A61B 5/7246 |

FOREIGN PATENT DOCUMENTS

| | | |
|---|---|---|
| CN | 107820410 A | 3/2018 |
| CN | 107907916 A | 4/2018 |
| CN | 108139790 A | 6/2018 |
| CN | 108337903 A | 7/2018 |
| CN | 110584632 A | 12/2019 |
| CN | 111568402 A | 8/2020 |
| CN | 107635456 B | 6/2021 |
| WO | 2009088799 A1 | 7/2009 |

OTHER PUBLICATIONS

Chinese Office Action dated Apr. 26, 2023; Chinese Application No. 202011208682.7.

* cited by examiner

WEARING STATE DETECTION METHOD, WEARING STATE DETECTION DEVICE AND WEARABLE DEVICE

PRIORITY

The present application constitutes a bypass continuation of International Application PCT/CN2020/126071, filed on Nov. 3, 2020, which is incorporated herein by reference in the entirety.

TECHNICAL FIELD

The present disclosure relates to the technical field of electronics, in particular, to a wearing state detection method, a wearing state detection device and a wearable device.

BACKGROUND

Currently, wearable devices such as smart watches, smart bracelets and TWS headphones have been widely used in fields of communication, entertainment, sports, health monitoring or the like. Due to a small volume and internal space of a wearable device, a tiny or small battery is generally used for power supply, resulting in limited standby time and operation time. Moreover, when the wearable device is used to detect physiological parameter information such as a heart rate, blood pressure, blood oxygen, etc. of a subject, it is required for the wearable device to be in a wearing state to obtain effective data results. Therefore, in order to save power consumption, prolong battery life, and ensure the accuracy of detection results of various physiological parameters, power-consuming functional modules such as those for heart rate detection can be turned on when the subject is wearing the wearable device and turned off when the subject is not wearing the wearable device. Therefore, it needs to accurately and efficiently detect a wearing state of the wearable device.

Presently, most of wearable devices adopt PPG (Photo Plethysmo Graphy) technologies to detect a heart rate, that is, a light source irradiates human skin, and since a volume of blood perfusion in subcutaneous tissue changes periodically with a pulse, absorption of incident light fluctuates periodically, which makes intensity of reflected light and a measured PPG signal change periodically. In this way, information indicating the human heart rate can be obtained.

Therefore, an existing method for determining whether the wearable device is worn is as follows. A PPG sensor is used to output an optical signal of a specific wavelength, the optical signal is received by the PPG sensor after being reflected by the human skin and converted into an electrical signal, and the electrical signal is amplified and filtered to obtain a PPG signal. If the PPG signal is a periodic signal and its frequency matches a human heart rate signal, it is determined that the wearable device is in a wearing state; and if the PPG signal is not the periodic signal, or its frequency does not match the human heart rate signal, it is determined that the wearable device is in a non-wearing state.

However, when the wearable device is quickly removed, and after removing, the PPG sensor faces a relatively stationary object under an indoor fluorescent lamp, the fluorescent lamp emits light at a specific frequency, the emitted light is received by the PPG sensor after being reflected by the object, and an electrical signal with multiple frequency components is output, and likewise, the electrical signal is also filtered to filter out high-frequency components and low-frequency components, and thus the obtained signal also fluctuates periodically, with a frequency matching with the human heart rate signal, as a result, it is determined that the wearable device is in the wearing state and the heart rate is detected continuously, thus an invalid heart rate detection result is output, resulting in additional power consumption.

SUMMARY

A purpose of the present disclosure is to overcome above-mentioned defects in the prior art, and to provide a wearing state detection method, a wearing state detection device and a wearable device, so as to improve accuracy of a wearing state detection result.

In a first aspect, an embodiment of the present disclosure provides a wearing state detection method for detecting a wearing state of a wearable device. The wearable device includes a light emitting unit and a light receiving unit, and the wearing state detection method includes:

emitting, by the light emitting unit, light of at least two different wavelengths to a subject in a time division manner;

receiving, by the light receiving unit, reflected light corresponding to light of each of the at least two different wavelengths after being reflected by the subject;

obtaining intensity of reflected light corresponding to the light of each of the at least two different wavelengths, respectively;

calculating a fluctuation range of a light intensity ratio, the light intensity ratio being a ratio between intensity of the reflected light corresponding to the light of the at least two different wavelengths received by a same light receiving unit; and determining that the wearable device is in a wearing state when the fluctuation range of the light intensity ratio is greater than or equal to a first threshold When the light of different wavelengths emitted by the light emitting unit irradiates a relatively stationary object, a proportion of light components with different wavelengths in the reflected light received by the light receiving unit remains almost unchanged and the light intensity ratio hardly fluctuates at this time. However, when the light of different wavelengths emitted by the light emitting unit irradiates the skin of a human body, since absorption and reflectivity of light of different wavelengths by the human body are different and blood flow and vasodilation in the subcutaneous tissue causes different periodic fluctuations in the absorption and reflectivity of light of different wavelengths by the human body, a proportion of light components with different wavelengths in the reflected light received by the light receiving unit also fluctuates, that is, the light intensity ratio fluctuates periodically. Therefore, by determining the fluctuation range of the light intensity ratio among various light components in the reflected light, it is possible to accurately distinguish whether the light emitting unit and the light receiving unit of the wearable device faces the human body or faces the relatively stationary object under a fluorescent lamp, thereby improving a rate of correctly response to the non-wearing state of the wearable device and accuracy of a wearing state detection result.

Optionally, the wearing state detection method further includes: determining that the wearable device is in a non-wearing state when the fluctuation range of the light intensity ratio is smaller than the first threshold.

Optionally, the wearing state detection method further includes, when the fluctuation range of the light intensity ratio is greater than or equal to the first threshold:
  determining that the wearable device is in a well wearing state when the fluctuation range of the light intensity ratio is smaller than a second threshold, the second threshold being greater than the first threshold.

Optionally, the wearing state detection method further includes: determining that the wearable device is in a bad wearing state when the fluctuation range of the light intensity ratio is greater than or equal to the second threshold.

Optionally, said obtaining the intensity of the reflected light corresponding to the light of the at least two different wavelengths further includes:
  acquiring an electrical signal output by the light receiving unit after receiving the reflected light corresponding to the light of each of the at least two different wavelengths, respectively, to obtain raw data of intensity of the reflected light;
  acquiring an electrical signal output by the light receiving unit after receiving ambient light to obtain raw data of intensity of the ambient light before and/or after the light emitting unit emits the light of at least two different wavelengths to the subject in a time division manner;
  eliminating ambient light component contained in the raw data of intensity of the reflected light by using the raw data of intensity of the ambient light; and
  calculating the intensity of the reflected light corresponding to the light of each of the at least two different wavelengths respectively based on the raw data of intensity of the reflected light with the ambient light component being eliminated.

Optionally, the light of the at least two different wavelengths includes green light and red light; or green light and infrared light; or green light, red light and infrared light.

In a second aspect, an embodiment of the present disclosure provides a wearing state detection device for detecting a wearing state of a wearable device. The wearing state detection device includes:
  a light emitting unit configured to emit light of at least two different wavelengths to a subject in a time division manner;
  a light receiving unit configured to receive reflected light corresponding to light of each of the at least two different wavelengths after being reflected by the subject;
  a signal processing module configured to obtain intensity of reflected light corresponding to the light of each of the at least two different wavelengths respectively, and calculating a fluctuation range of a light intensity ratio, the light intensity ratio being a ratio between intensity of the reflected light corresponding to the light of the at least two different wavelengths received by a same light receiving unit; and
  a wearing state determination module configured to determine that the wearable device is in a wearing state when the fluctuation range of the light intensity ratio is greater than or equal to a first threshold.

The light emitting unit is configured to emit detection light of at least two different wavelengths to the subject in a time division manner, and the detection light of different wavelengths are received by the light receiving unit after being reflected by the subject. By determining the fluctuation range of the light intensity ratio among various light components in the reflected light, it is possible to accurately distinguish whether the light emitting unit and the light receiving unit of the wearable device faces the human body or faces the relatively stationary object under a fluorescent lamp, thereby improving a rate of correctly response to the non-wearing state of the wearable device and accuracy of a wearing state detection result.

Optionally, the wearing state determination module is further configured to:
  determine that the wearable device is in a non-wearing state when the fluctuation range of the light intensity ratio is smaller than the first threshold.

Optionally, the wearing state determination module is further configured to, when the fluctuation range of the light intensity ratio is greater than or equal to the first threshold:
  determine that the wearable device is in a well wearing state when the fluctuation range of the light intensity ratio is smaller than a second threshold, the second threshold being greater than the first threshold.

Optionally, the wearing state determination module is further configured to:
  determine that the wearable device is in a bad wearing state when the fluctuation range of the light intensity ratio is greater than or equal to the second threshold.

Optionally, the signal processing module is further configured to:
  acquire an electrical signal output by the light receiving unit after receiving the reflected light corresponding to the light of each of the at least two different wavelengths respectively, to obtain raw data of intensity of the reflected light;
  acquire an electrical signal output by the light receiving unit after receiving ambient light to obtain raw data of intensity of the ambient light before and/or after the light emitting unit emits the light of the at least two different wavelengths to the subject in a time division manner;
  eliminate ambient light component contained in the raw data of intensity of the reflected light by using the raw data of intensity of the ambient light; and
  calculate the intensity of the reflected light corresponding to the light of each of the at least two different wavelengths respectively based on the raw data of intensity of the reflected light with the ambient light component being eliminated.

Optionally, the light of the at least two different wavelengths includes green light and red light; or green light and infrared light; or green light, red light and infrared light.

In a third aspect, an embodiment of the present disclosure provides a wearable device, which includes: a light emitting unit configured to emit light of at least two different wavelengths to a subject in a time division manner;
  a light receiving unit configured to receive reflected light corresponding to light of each of the at least two different wavelengths after being reflected by the subject;
  a signal processing module configured to obtain intensity of reflected light corresponding to the light of each of the at least two different wavelengths respectively, and calculating a fluctuation range of a light intensity ratio, the light intensity ratio being a ratio between intensity of the reflected light corresponding to the light of the at least two different wavelengths received by a same light receiving unit; and
  a wearing state determination module configured to determine that the wearable device is in a wearing state when the fluctuation range of the light intensity ratio is greater than or equal to a first threshold.

Optionally, the wearing state determination module is further configured to: determine that the wearable device is in a non-wearing state when the fluctuation range of the light intensity ratio is smaller than the first threshold.

Optionally, the wearing state determination module is further configured to, when the fluctuation range of the light intensity ratio is greater than or equal to the first threshold:
  determine that the wearable device is in a well wearing state when the fluctuation range of the light intensity ratio is smaller than a second threshold, the second threshold being greater than the first threshold.

Optionally, the wearing state determination module is further configured to:
  determine that the wearable device is in a bad wearing state when the fluctuation range of the light intensity ratio is greater than or equal to the second threshold.

Optionally, the signal processing module is further configured to:
  acquire an electrical signal output by the light receiving unit after receiving the reflected light corresponding to the light of each of the at least two different wavelengths respectively, to obtain raw data of intensity of the reflected light;
  acquire an electrical signal output by the light receiving unit after receiving ambient light to obtain raw data of intensity of the ambient light before and/or after the light emitting unit emits the light of the at least two different wavelengths to the subject in a time division manner;
  eliminate ambient light component contained in the raw data of intensity of the reflected light by using the raw data of intensity of the ambient light; and
  calculate the intensity of the reflected light corresponding to the light of each of the at least two different wavelengths respectively based on the raw data of intensity of the reflected light with the ambient light component being eliminated.

Optionally, the light of the at least two different wavelengths includes green light and red light; or green light and infrared light; or green light, red light and infrared light.

The wearable device can accurately distinguish whether the light emitting unit and the light receiving unit faces the human body or faces the relatively stationary object under a fluorescent lamp, thereby improving a rate of correctly response to the non-wearing state of the wearable device and accuracy of a wearing state detection result.

BRIEF DESCRIPTION OF DRAWINGS

One or more embodiments are illustrated by corresponding figures in the drawings, which do not constitute a limitation on the present disclosure. Components with same reference numerals in the drawings are similar components, and unless otherwise stated, the figures in the drawings do not constitute a scale limitation.

DESCRIPTION OF EMBODIMENTS

The technical solution in the embodiments of the present disclosure will be described in detail in the following in combination with the drawings. Obviously, the described embodiments merely some, rather all of the embodiments of the present disclosure.

Unless a specified order is clearly stated in a context of the present disclosure, processing steps described herein may be performed differently from the specified order described in the embodiments, that is, respective steps may be performed in the specified order, substantially simultaneously, in a reverse order, or in a different order.

Terminologies used in the present disclosure is for a purpose of describing specific embodiments only, and is not intended to limit the present disclosure. A singular form of "a", "said" and "the" used in the present disclosure and the appended claims are also intended to include a plural form, unless other meaning is clearly indicated in the context.

In addition, terms such as "first" and "second" are merely used to distinguish similar objects, and cannot be understood as indicating or implying relative importance or implicitly indicating a number of indicated technical features. Thus, the features defined with "first", "second" and the like may explicitly or implicitly include one or more of these features.

In a first aspect, an embodiment of the present disclosure provides a wearing state detection method for detecting a wearing state of a wearable device such as a smart watch, a smart bracelet, a smart armband, a smart finger ring, a TWS headphone, etc., and a type of the wearable device is not limited thereto.

Figure 1:
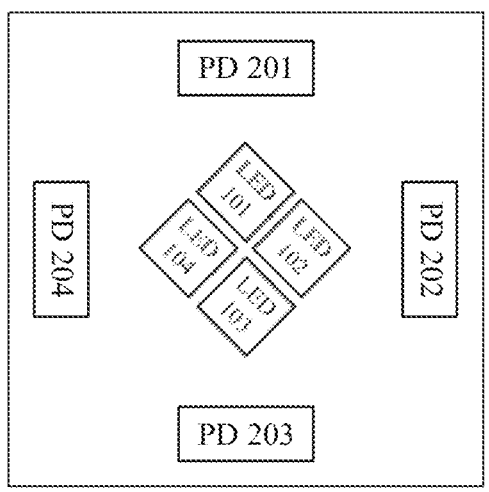
FIG. 1 is a schematic diagram of a positional relationship between a light emitting unit and a light receiving unit of a wearable device according to an embodiment of the present disclosure.

As is shown in FIG. 1, a schematic diagram of a positional relationship between a light emitting unit and a light receiving unit of a wearable device according to an embodiment of the present disclosure is shown. It includes four light emitting units, all of which are light emitting diodes (LEDs), and specifically are an infrared LED 101, a green LED 102, a red LED 103 and a green LED 104; and four light receiving units, all of which are photo-diodes (PD), and specifically are PD 201, PD 202, PD 203 and PD 204.

It should be noted that the type, number and positional relationship of the light emitting units and the light receiving units are not limited thereto. Moreover, a type and number of light sources emitted by the light emitting unit can be selected according to actual application scenarios or target requirements, and there are at least two types of light sources. For example, in order to save power consumption, only one green LED and one red LED can be provided, or only one green LED and one infrared LED can be provided. Or, in order to improve accuracy of a wearing state detection result, a green LED, a red LED and an infrared LED can be provided. Or, appropriate types and number of light sources are firstly provided according to requirements of other detection modules (such as a heart rate detection module, a blood oxygen detection module, etc.), and only part of the light sources are selected when the wearing state is being detected. The light emitting unit can also be a light emitting element formed by packaging a plurality of different light sources together. In addition, the number of the light receiving units may be one or multiple.

Figure 2:
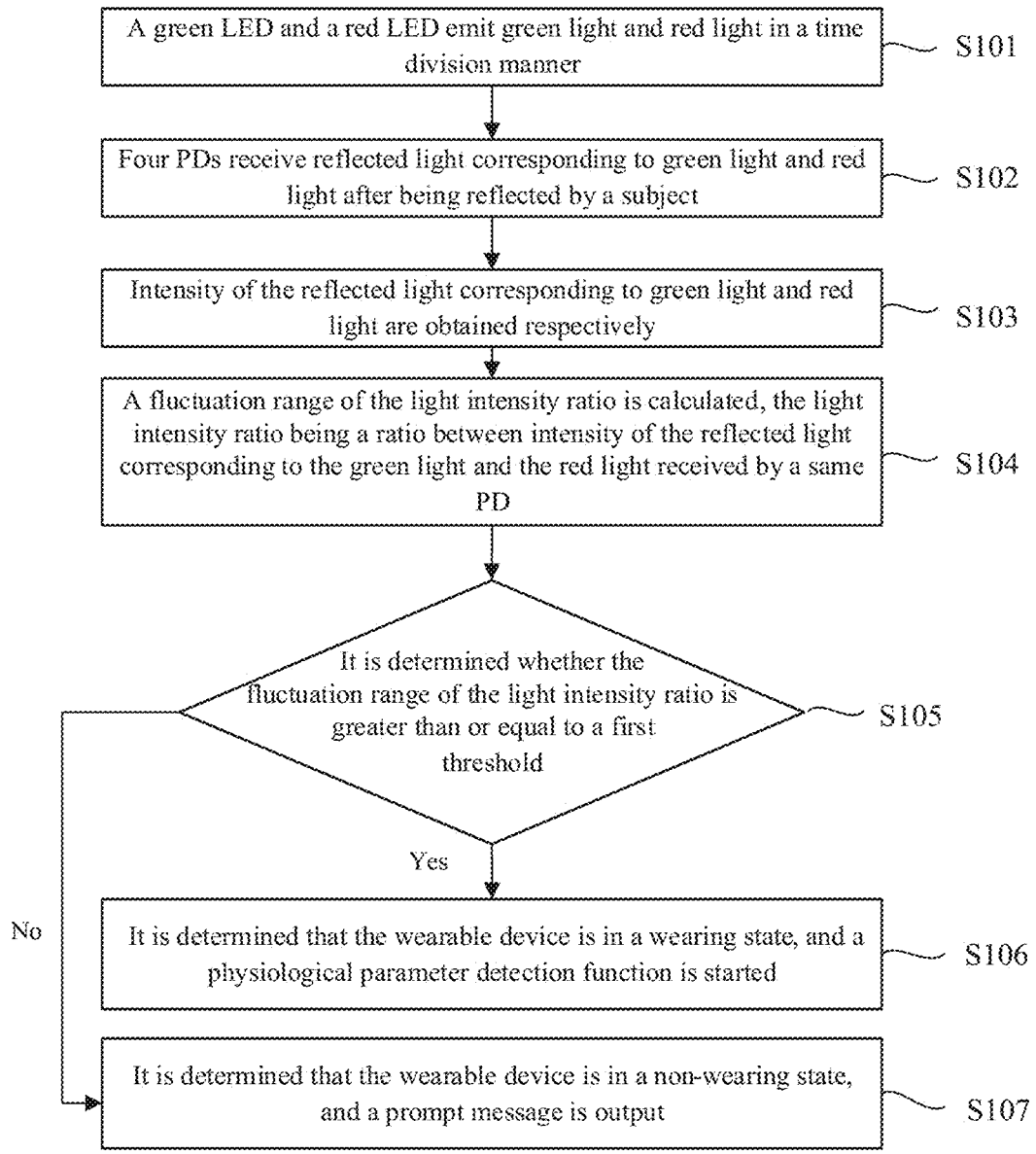
FIG. 2 is a flowchart of a wearing state detection method according to an embodiment of the present disclosure.

For ease of clear description, the method for detecting the wearing state according to an embodiment of the present disclosure will be described below in an example that the green LED 102 and the red LED 103 in FIG. 1 emit green light and red light in a time division manner, and the four PDs (PD 201, PD 202, PD 203 and PD 204) receive reflected light corresponding to the green light and the red light respectively. As shown in FIG. 2, a flowchart of a wearing state detection method according to an embodiment of the present disclosure is shown. Specifically, the method includes steps S101 to S107.

In S101, a green LED 102 and a red LED 103 emit green light and red light in a time division manner.

Here, it can be provided that the green LED 102 firstly emits green light, and after green light emission is finished, the red LED 103 emits red light; or, it can be provided that the red LED 103 firstly emits red light, and after red light emission is finished, the green LED 102 emits green light, which is not limited in the embodiments of the present disclosure.

In S102, four PDs receive reflected light corresponding to green light and red light after being reflected by a subject.

PD 201, PD 202, PD 203 and PD 204 receive the corresponding reflected light corresponding to the above-mentioned green light and red light after being reflected by a subject, and convert the received reflected light into respective electrical signals for output.

In S103, intensity of the reflected light corresponding to green light and red light are obtained respectively.

The intensity of the reflected light corresponding to the green light received by PD 201, PD 202, PD 203 and PD 204 are respectively denoted as $G_1$, $G_2$, $G_3$ and $G_4$. The intensity of the reflected light corresponding to the red light received by PD 201, PD 202, PD 203 and PD 204 are respectively denoted as $R_1$, $R_2$, $R_3$ and $R_4$.

In S104, a fluctuation range of the light intensity ratio is calculated. The light intensity ratio is a ratio between intensity of the reflected light corresponding to the green light and the red light received by a same PD.

Specifically, the light intensity ratio is calculated by using the light intensity $G_1$, $G_2$, $G_3$ and $G_4$ of the reflected light corresponding to the green light and the light intensity $R_1$, $R_2$, $R_3$ and $R_4$ of the reflected light corresponding to the red light to obtain four light intensity ratios $R_1/R_2/G_2$, $R_3/G_3$ and $R_4/G_4$.

The fluctuation range of the light intensity ratio refers to a difference between a maximum value and a minimum value when the light intensity ratio fluctuates in a period of time. If the fluctuation of light intensity ratio is large, it indicates that the fluctuation range of light intensity ratio is intense; and if the fluctuation range of the light intensity ratio is small or approximately zero, it indicates that the fluctuation of the light intensity ratio is gentle or hardly generated.

Since four PDs are located at different positions around the green LED 102 and the red LED 103, that is, their directions and distances from the green LED 102 and the red LED 103 are different, the intensity of the received reflected light is also different. By limiting calculation of the light intensity ratio between the reflected light corresponding to the green light and red light received by the same PD, a more objective and accurate light intensity ratio can be obtained, which facilitates improving the accuracy of the wearing state detection result.

In S105, it is determined whether the fluctuation range of the light intensity ratio is greater than or equal to a first threshold.

The first threshold can be set to be a specific value, and when each of fluctuation ranges of the four light intensity ratios are each greater than or equal to this value, the process proceeds to step S106; and when at least one of fluctuation ranges of the four light intensity ratios is smaller than this value, the process proceeds to step S107.

Or, the first threshold can be set to four specific values, and these four specific values are used as comparison references of the fluctuation ranges of the four light intensity ratios, and when each of fluctuation ranges of the four light intensity ratios is greater than or equal to a respective comparison reference, the process proceeds to step S106; and when at least one of fluctuation ranges of the light intensity ratios is smaller than a respective comparison reference, the process proceeds to step S107.

In S106, it is determined that the wearable device is in a wearing state, and a physiological parameter detection function is started.

If it is determined that the wearable device is in the wearing state, the physiological parameter detection function such as heart rate detection, blood oxygen detection or blood pressure detection can be started.

In S107, it is determined that the wearable device is in a non-wearing state, and a prompt message is output.

If it is determined that the wearable device is in the non-wearing state, a prompt message is output to remind a user to wear the wearable device or wear it correctly, so as to obtain an accurate and effective physiological parameter detection result, thereby avoiding blindly starting the physiological parameter detection function in the non-wearing state, resulting in a wrong return value and unnecessary power consumption.

It should be noted that the operations that can be performed when the wearable device is determined to be in the wearing or non-wearing state are not limited to this. Other instructions of the user can also be executed if the wearable device is determined to be in the wearing state, or execution of a certain function operation can be stopped if the wearable device is determined to be in the non-wearing state.

Because the human body's absorption to green light is higher than that to red light, and the human body's transmission to green light is weaker than that to red light, when the green light is used for detection, only changes of superficial tissues or blood vessels under the skin can be reflected, while when the red light is used for detection, changes of deeper tissues or blood vessels can be reflected. Therefore, when green light and red light illuminate the human body, changes of blood volume in superficial tissues and deep tissues cause different periodic changes in the absorption to the green light and the red light, thus making the light intensity ratio between reflected light corresponding to the green light and reflected light corresponding to the red light fluctuate, that is, the light intensity ratio will have a certain fluctuation range. However, the absorption to the green light and the red light of a stationary object is basically unchanged, so when the green light and red light illuminate a stationary object under a fluorescent lamp, with superposition of ambient light formed by the fluorescent lamp, the intensity of the reflected light corresponding to the green light and red light presents roughly a same periodic change, and the fluctuation range of the light intensity ratio at this time is very small, even approximately zero. Therefore, by determining a magnitude of the fluctuation range of the light intensity ratio, it is possible to accurately distinguish whether the light emitting unit and the light receiving unit of the wearable device faces the human body or faces the relatively stationary object, thereby improving a rate of correctly response to the non-wearing state of the wearable device and accuracy of a wearing state detection result.

As a possible implementation, the following methods can be adopted to obtain the intensity of the reflected light corresponding to the green light and the red light respectively:

Electrical signals output by the four PDs after receiving the reflected light corresponding to the green light and the red light respectively are acquired, so as to obtain respective raw data of intensity of the reflected light.

Electrical signals output by four PDs after receiving ambient light are acquired to obtain raw data of intensity of the ambient light before and/or after the green LED 102 and the red LED 103 emit the green light and the red light in a time division manner.

Ambient light component contained in the raw data of intensity of the reflected light is eliminated by using the raw data of intensity of the ambient light.

The intensity of the reflected light corresponding to the green light and the red light respectively is calculated according to the raw data of intensity of the reflected light with the ambient light component being eliminated.

Since the wearable device may not be closely attached with the human skin in an actual wearing process, there may be a gap between the PD and the subject, resulting in light leakage, and then the light signal received by the PD also contains ambient light noise (such as sunlight or the indoor fluorescent lamp, etc.), which may lead to errors in a calculation result of the light intensity, thus affecting a calculation result of the light intensity ratio. Therefore, with the ambient light noise being eliminated, the accuracy of the wearing state detection result can be further improved.

For ease of clear description, obtaining of the intensity of the reflected light corresponding to the green light and the red light respectively is explained in an example that the green LED 102 emits the green light firstly, followed by that the red LED 103 emits the red light, and the PD 201 receives the reflected light corresponding to the green light and the red light respectively.

Figure 3:
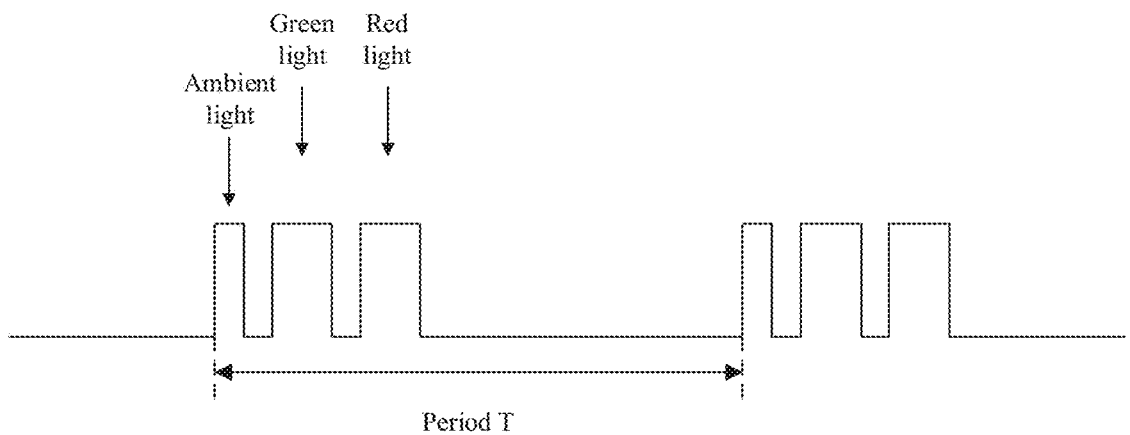
FIG. 3 is a schematic diagram of a sampled signal waveform corresponding to an ambient light eliminating method according to an embodiment of the present disclosure.
Figure 4:
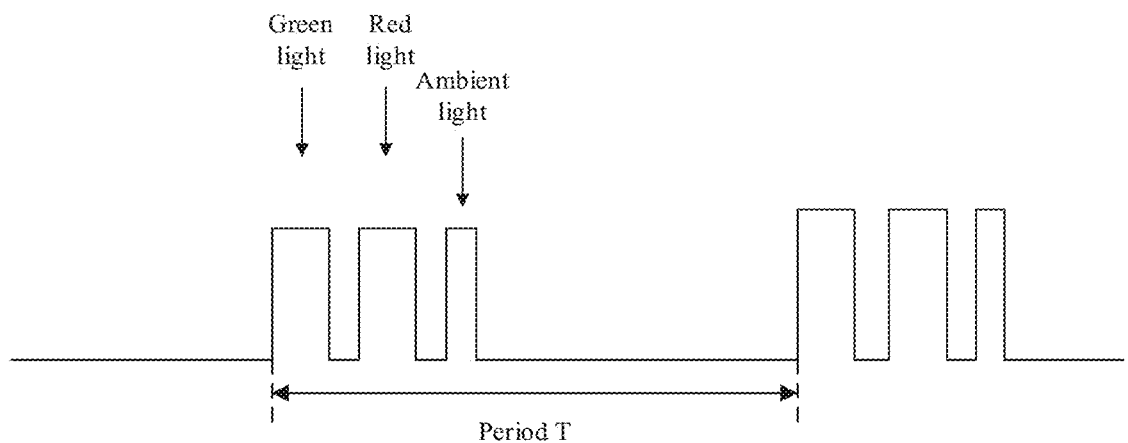
FIG. 4 is a schematic diagram of a sampled signal waveform corresponding to another ambient light eliminating method according to an embodiment of the present disclosure.

An electrical signal output by the PD 201 after receiving the reflected light corresponding to the green light is acquired to obtain raw data of intensity of the reflected light $G_{rawdata1}$. An electrical signal output by the PD 201 after receiving the reflected light corresponding to the red light is acquired to obtain raw data of intensity of the reflected light $R_{rawdata1}$. The PD 201 receives the ambient light before or after the green LED 102 and the red LED 103 emit the green light and the red light, and an electrical signal output by the PD 201 after receiving the ambient light is acquired to correspondingly obtain raw data of intensity of the ambient light $AL_{rawdata1}$ or $AL_{rawdata2}$. In this way, a sampled signal waveform diagram as shown in FIG. 3 or FIG. 4 respectively is obtained.

At this time, the ambient light components contained in the raw data of intensity of the reflected light $G_{rawdata1}$ or $R_{rawdata1}$ can be eliminated according to following equations, that is, a first-order ambient light elimination is performed:

$$G_{rawdata1}' = G_{rawdata1} - AL_{rawdata1} \quad \text{(Equation 1A); and}$$

$$R_{rawdata1}' = R_{rawdata1} - AL_{rawdata1} \quad \text{(Equation 2A); or}$$

$$G_{rawdata1}' = G_{rawdata1} - AL_{rawdata2} \quad \text{(Equation 1B); and}$$

$$R_{rawdata1}' = R_{rawdata1} - AL_{rawdata2} \quad \text{(Equation 2B).}$$

Here, $G_{rawdata1}'$ is the raw data of intensity of the reflected light after the ambient light component in $G_{rawdata1}$ is eliminated; and $R_{rawdata1}'$ is the raw data of intensity of the reflected light after the ambient light component in $R_{rawdata1}$ is eliminated.

Figure 5:
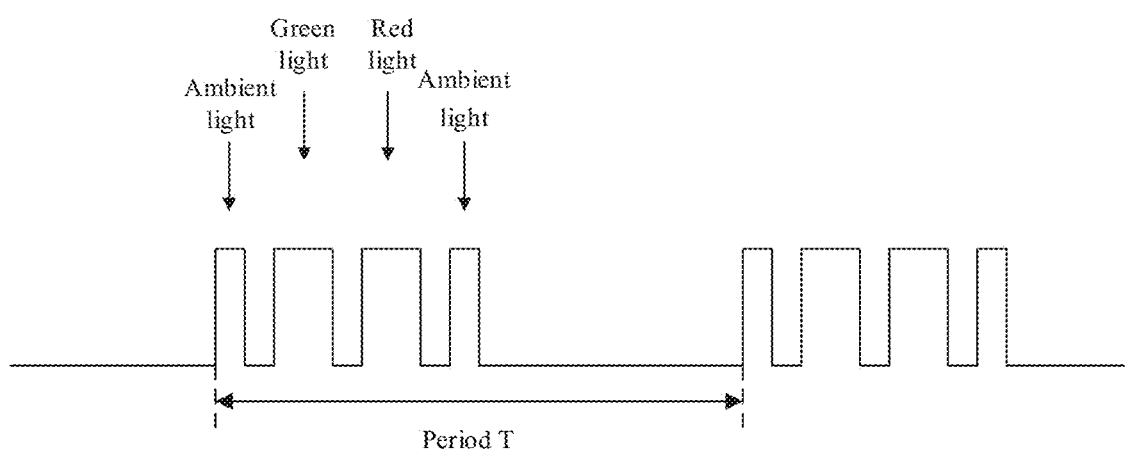
FIG. 5 is a schematic diagram of a sampled signal waveform corresponding to yet another ambient light eliminating method according to an embodiment of the present disclosure.

Or, the PD 201 receives the ambient light both before and after the green LED 102 and the red LED 103 emit the green light and the red light, and electrical signals output by the PD 201 after receiving the ambient light are acquired to correspondingly obtain raw data of intensity of the ambient light $AL_{rawdata1}$ and $AL_{rawdata2}$. In this way, a sampled signal waveform diagram as shown in FIG. 5 is obtained.

At this time, the ambient light components contained in the raw data of intensity of the reflected light $G_{rawdata1}$ or $R_{rawdata1}$ can be eliminated according to following equations, that is, a second-order ambient light elimination is performed:

$$G'_{rawdata1} = G_{rawdata1} - \frac{AL_{rawdata1} + AL_{rawdata2}}{2}; \quad \text{(Equation 3)}$$

$$R'_{rawdata1} = R_{rawdata1} - \frac{AL_{rawdata1} + AL_{rawdata2}}{2} \quad \text{(Equation 4)}$$

Compared with the first-order ambient light elimination, a higher ambient light suppression ratio can be obtained with the second-order ambient light elimination, thereby achieving more accurate calculation of the intensity of the reflected light corresponding to the green light and the red light respectively.

It should be noted that, the electrical signal output by the PD 201 after receiving the ambient light can be acquired for several times before and/or after the green LED 102 and the red LED 103 emit the green light and the red light, so as to obtain a higher ambient light suppression ratio. Or, the electrical signal output by the PD 201 after receiving the ambient light can be acquired in an interval between the green LED 102 emitting the green light and the red LED 103 emitting the red light.

It should be noted that a process of acquiring the electrical signal output by the PD 201 after receiving the ambient light means that the PD 201 receives the ambient light when the green LED 102 and the red LED 103 do not emit light, converts the ambient light into an electrical signal for output, and then the electrical signal is acquired.

The PD 201 can output a respective electrical signal after receiving the reflected light corresponding to the green light and red light respectively, and signal processing performed on these electrical signals may include: filtering, gain conversion, analog-to-digital (A/D) conversion, and ambient light elimination, so as to obtain the raw data of intensity $G_{rawdata1}'$ and $R_{rawdata1}'$ of the reflected light after the ambient light component is eliminated. Herein, the gain conversion can be understood as amplifying the signal. Therefore, the intensity of the reflected light corresponding to the green light and the red light can be calculated by using $G_{rawdata1}'$ and $R_{rawdata1}'$ according to following equations:

$$G_1 = \frac{G_{rawdata1}' - \text{offset}}{\text{Gain}_1 \cdot \text{Current}_1} \quad \text{(Equation 5)}$$

$$R_1 = \frac{R_{rawdata1}' - \text{offset}}{\text{Gain}_2 \cdot \text{Current}_2} \quad \text{(Equation 6)}$$

Herein, offset is a preset offset, which is used to obtain the raw data of intensity of the reflected light with an appropriate numerical value; $\text{Gain}_1$ and $\text{Gain}_2$ are signal amplification factors at which the gain conversion is performed on the electrical signal output by the PD 201 after receiving the reflected light corresponding to the green light and the red light respectively; and $\text{Current}_1$ and $\text{Current}_2$ are supply currents of the green LED 102 and the red LED 103, respectively. Values of Gain and Current can be regularly monitored when the raw data of intensity of the reflected light is acquired. For example, considering a limited number of calculation, Values of Gain and Current can be obtained once every seven frames of data.

It should be noted that PD 202, PD 203 and PD 204 can obtain light intensity $G_2$, $G_3$ and $G_4$ of the reflected light corresponding to the green light and light intensity $R_2$, $R_3$ and $R_4$ of the reflected light corresponding to the red light based on a substantially same method.

Figure 6:
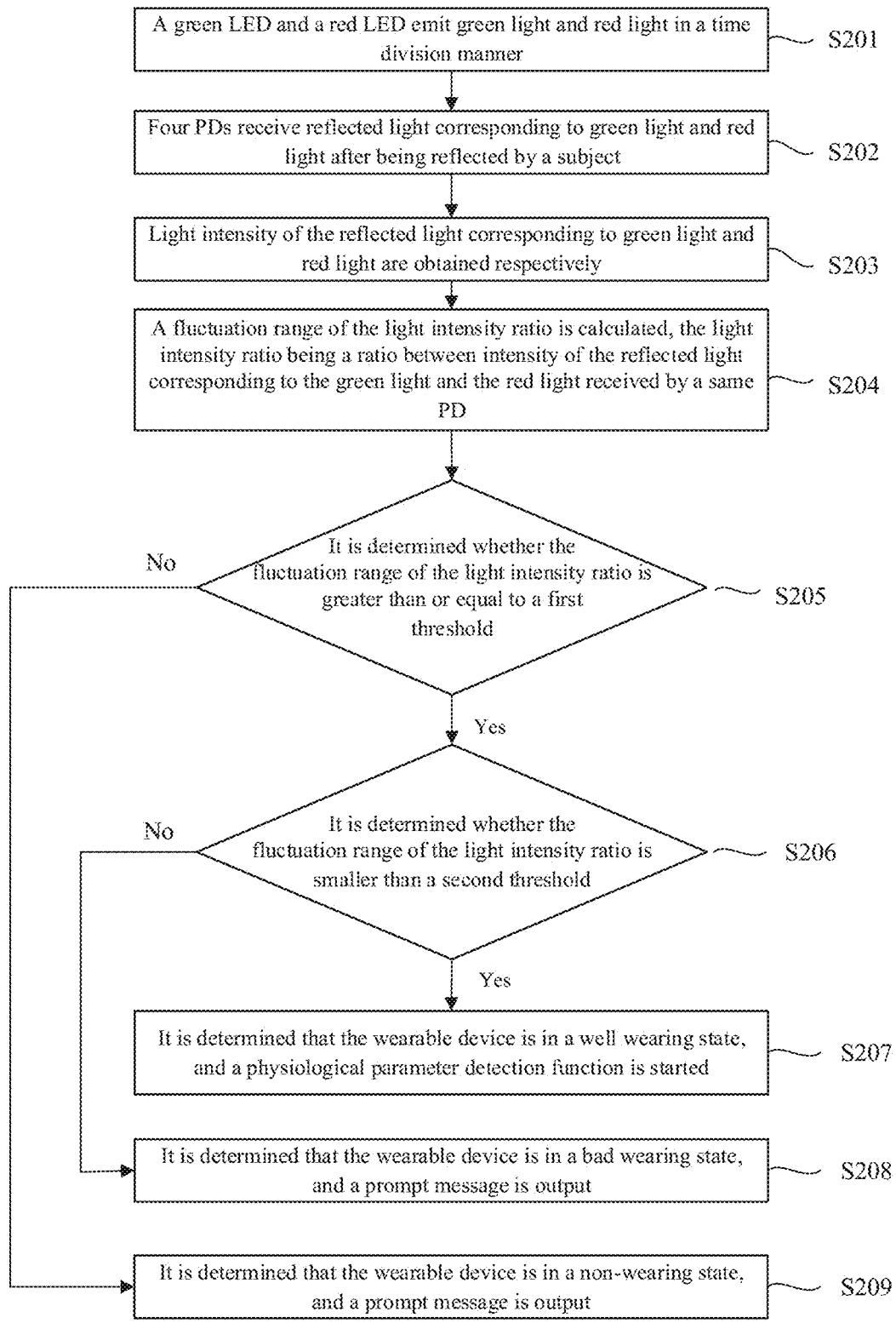
FIG. 6 is a flowchart of another wearing state detection method according to an embodiment of the present disclosure.

As shown in FIG. 6, a flowchart of another wearing state detection method according to an embodiment of the present disclosure is shown. When the fluctuation range of the light intensity ratio is greater than or equal to the first threshold, that is, when it is determined that the wearable device is in a wearing state, a wearing quality of the wearable device can be further determined, which specifically includes following steps.

Steps S201 to S205 are the same as steps S101 to S105, respectively, and when a determination result of step S205 is YES, the process proceeds to step S206; and when the determination result of step S205 is NO, the process proceeds to step S209.

In S206, it is determined whether the fluctuation range of the light intensity ratio is smaller than a second threshold.

Here, the second threshold can be set to be a specific value, and when each of fluctuation ranges of the four light intensity ratios is smaller than this value, the process proceeds to step S207; and when at least one of fluctuation ranges of the four light intensity ratios is greater than or equal to this value, the process proceeds to step S208

Or, the second threshold can be set to four specific values, and these four specific values are used as comparison references of fluctuation ranges of the four light intensity ratios, and when the each of fluctuation ranges of the four light intensity ratios is smaller than a respective comparison reference, the process proceeds to step S207; and when at least one of fluctuation ranges of the four light intensity ratios is greater than or equal to a respective comparison reference, the process proceeds to step S208.

In S207, it is determined that the wearable device is in a well wearing state, and a physiological parameter detection function is started.

If it is determined that the wearable device is in a wearing state, the physiological parameter detection function such as heart rate detection, blood oxygen detection or blood pressure detection can be started.

In S208, it is determined that the wearable device is in a bad wearing state, and a prompt message is output.

If it is determined that the wearable device is in a bad wearing state, a prompt message can be output to remind the user to wear the wearable device tightly or stably, so as to obtain a more accurate wearing state detection result.

In S209, it is determined that the wearable device is in a non-wearing state.

If it is determined that the wearable device is in a non-wearing state, a prompt message is output to remind a user to wear the wearable device or wear it correctly, so as to obtain an accurate and effective physiological parameter detection result, thereby avoiding blindly starting the physiological parameter detection function in the non-wearing state, resulting in a wrong return value and unnecessary power consumption.

The first threshold and the second threshold can be determined by acquiring fluctuation ranges of the light intensity ratio of the wearable device in various wearing states in advance. For example, a machine learning can be used to analyze and process the acquired fluctuation ranges of the light intensity ratio in advance, so as to determine initial values of the first threshold and the second threshold which can adapt to a basic application. By continuously acquiring relevant data of the fluctuation ranges of the light intensity ratio generated in the subject's subsequent use of the wearable device, values of the first threshold and the second threshold can be iteratively updated, so as to further improve individual adaptability and the accuracy of the wearing state detection result.

Figure 7A:
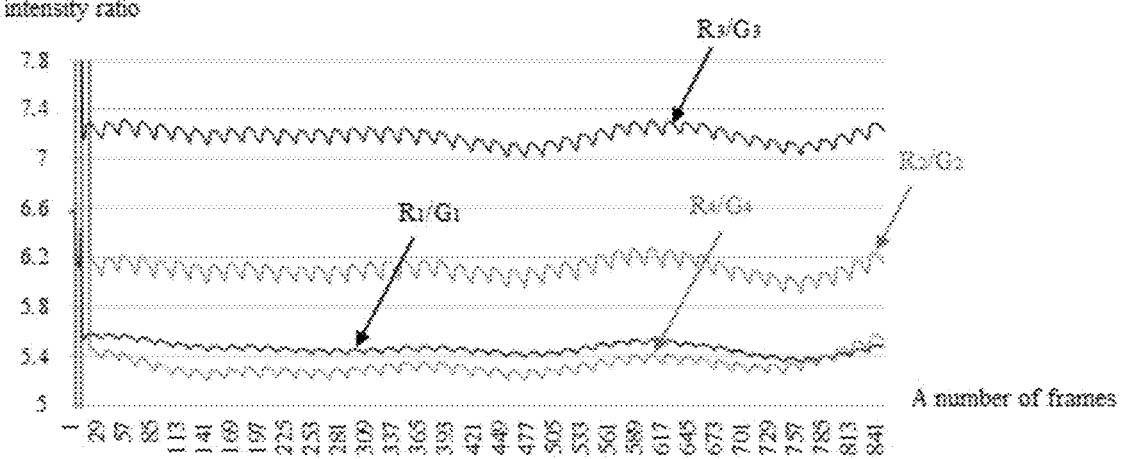
FIGS. 7(a) to 7(c) are schematic diagrams of fluctuation states of a light intensity ratio in three wearing states when the light emitting unit emits green light and red light in a time division manner according to an embodiment of the present disclosure.
Figure 7B:
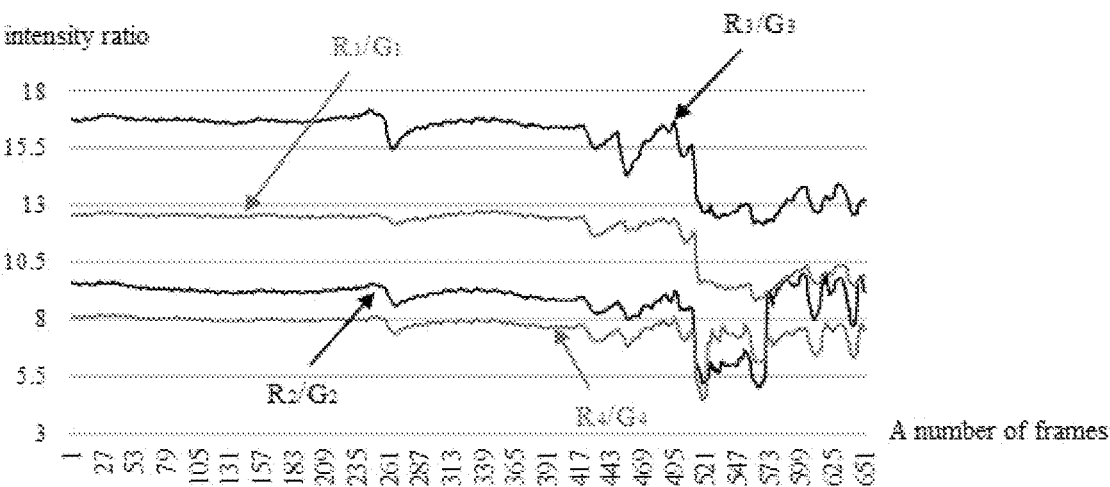
Figure 7C:
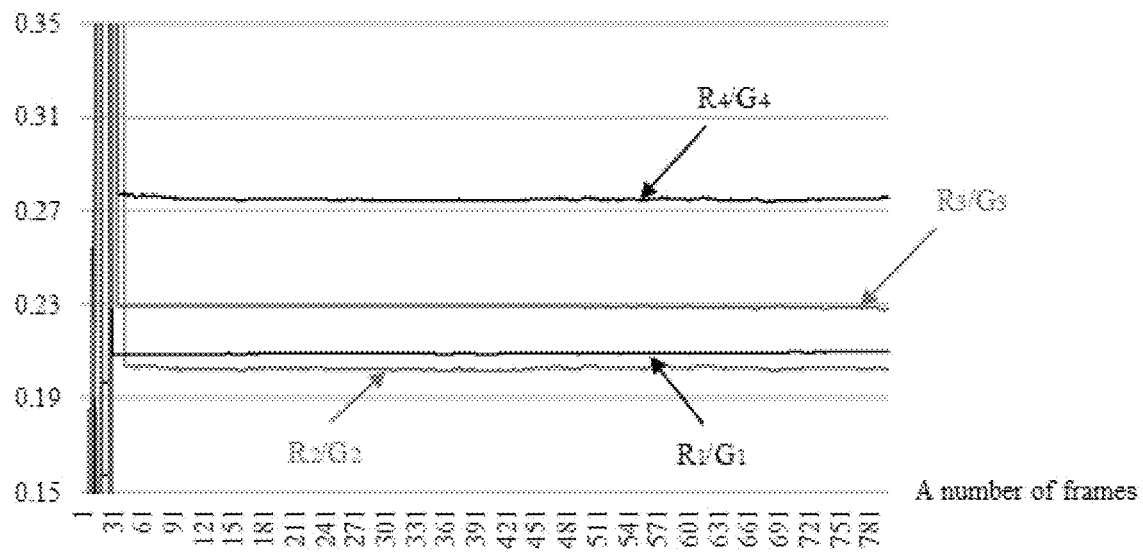

As is shown in FIG. 7, schematic diagrams of fluctuation states of a light intensity ratio in three wearing states when the light emitting unit emits the green light and the red light in a time division manner according to an embodiment of the present disclosure are shown, with a horizontal axis indicating a number of frames acquired and a vertical axis indicating the light intensity ratio.

Specifically, as shown in FIG. 7(*a*), it is a schematic diagram of fluctuation of the light intensity ratios in a resting state, that is, when the wearable device is in a well wearing state. After the light is stabilized, the four light intensity ratios present a certain fluctuation. At this time, the fluctuation ranges of the four light intensity ratios are as follows: $R_1/G_1$ is 0.32, $R_2/G_2$ is 0.41, $R_3/G_3$ is 0.31 and $R_4/G_4$ is 0.33, respectively.

As shown in FIG. 7(*b*), it is a schematic diagram of fluctuation of the light intensity ratios for the subject performing exercise aerobics, that is, when the wearable device is in a bad wearing state. It can be seen that the four light intensity ratios fluctuate violently, and the fluctuation ranges of the four light intensity ratios are as follows: $R_1/G_1$ is 4.51, $R_2/G_2$ is 5.13, $R_3/G_3$ is 5.26, and $R_4/G_4$ is 4.13, respectively.

As shown in FIG. 7(*c*), it is a schematic diagram of fluctuation of the light intensity ratios with the four PDs facing a blue notebook which is relatively stationary, that is, when the wearable device is in a non-wearing state. After the light is stabilized, the four light intensity ratios hardly fluctuate. At this time, the fluctuation ranges of the four light intensity ratios are as follows: $R_1/G_1$ is 0.003, $R_2/G_2$ is 0.003, $R_3/G_3$ is 0.003, and $R_4/G_4$ is 0.003.

It can be seen that in three different wearing states, the fluctuation ranges of four light intensity ratios are quite different, so we can accurately determine the wearing state of the wearable device by distinguishing the fluctuation ranges of the light intensity ratios.

As a possible implementation, the red light in the above embodiments can be replaced with infrared light. As is shown in FIG. 8, schematic diagrams of fluctuation states of a light intensity ratio in three wearing states when the light emitting unit emits green light and infrared light in a time division manner according to an embodiment of the present disclosure are shown, with a horizontal axis indicating a number of frames acquired and a vertical axis indicating the light intensity ratio.

The intensity of the reflected light corresponding to the infrared light received by the PD 201, PD 202, PD 203 and PD 204 are recorded as $IR_1$, $IR_2$, $IR_3$ and $IR_4$, and the four light intensity ratios $IR_1/G_1$, $IR_2/G_2$, $IR_3/G_3$ and $IR_4/G_4$ are calculated accordingly.

Figure 8A:
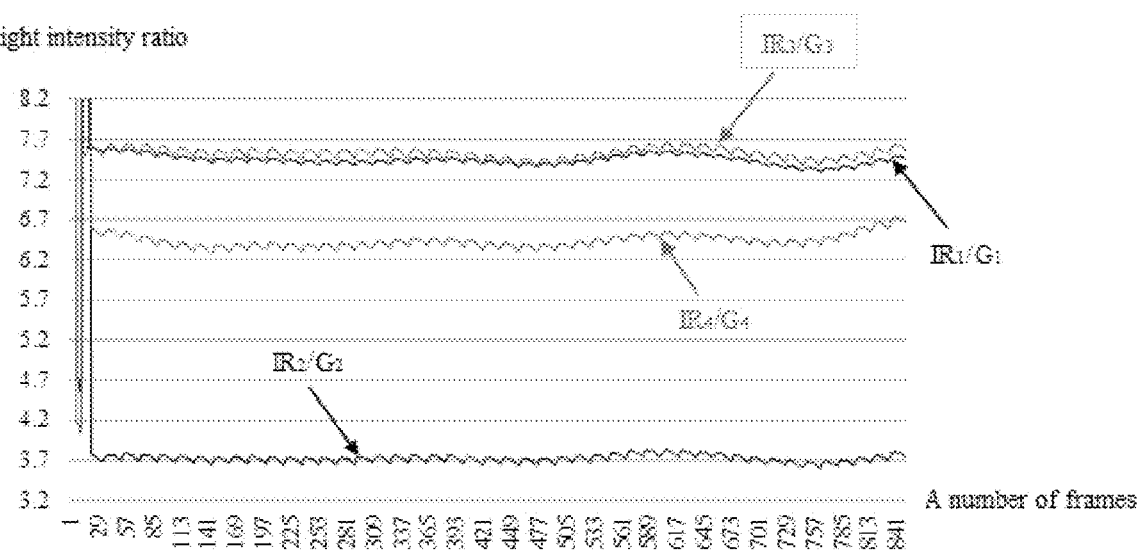
FIGS. 8(a) to 8(c) are schematic diagrams of fluctuation states of a light intensity ratio in three wearing states when the light emitting unit emits green light and infrared light in a time division manner according to an embodiment of the present disclosure.

Specifically, as shown in FIG. 8(a), it is a schematic diagram of fluctuation of the light intensity ratios in a resting state, that is, when the wearable device is in a well wearing state. After the light is stabilized, the four light intensity ratios present a certain fluctuation. At this time, the fluctuation ranges of the four light intensity ratios are as follows: $IR_1/G_1$ is 0.35, $IR_2/G_2$ is 0.37, $IR_3/G_3$ is 0.41 and $IR_4/G_4$ is 0.38, respectively.

Figure 8B:
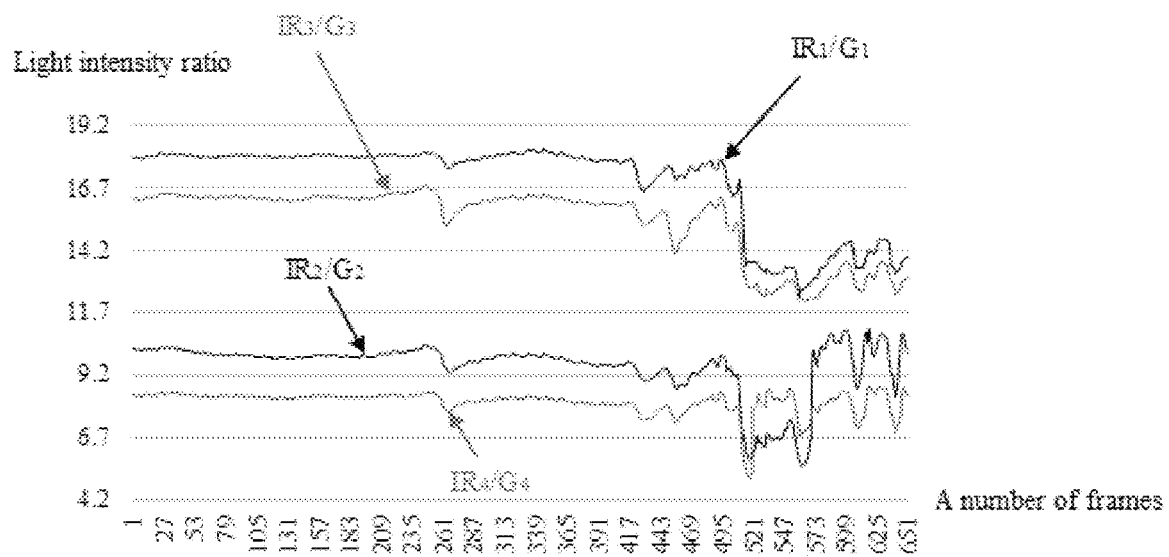

As shown in FIG. 8(b), it is a schematic diagram of fluctuation of the light intensity ratios for the subject performing exercise aerobics, that is, when the wearable device is in a bad wearing state. It can be seen that the four light intensity ratios fluctuate violently, and the fluctuation ranges of the four light intensity ratios are as follows: $IR_1/G_1$ is 5.73, $IR_2/G_2$ is 5.77, $IR_3/G_3$ is 5.13, and $IR_4/G_4$ is 3.98, respectively.

Figure 8C:
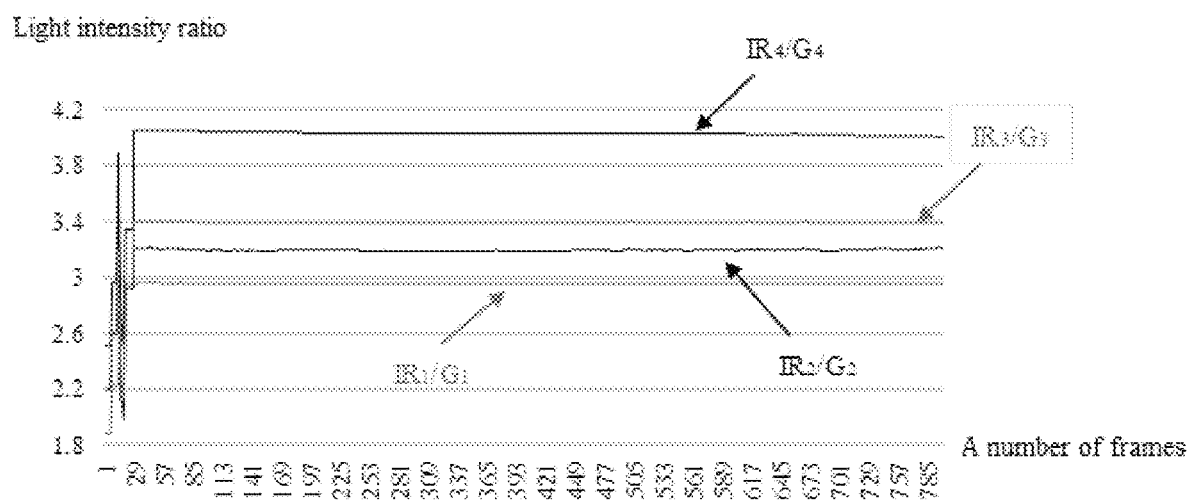

As shown in FIG. 8(c), it is a schematic diagram of fluctuation of the light intensity ratios with the four PDs facing a blue notebook which is relatively stationary, that is, when the wearable device is in a non-wearing state. After the light is stabilized, the four light intensity ratios hardly fluctuate. At this time, the fluctuation ranges of the four light intensity ratios are as follows: $IR_1/G_1$ is 0.015, $IR_2/G_2$ is 0.042, $IR_3/G_3$ is 0.023, and $IR_4/G_4$ is 0.071, respectively.

Therefore, when the light source is combined with the green light and the infrared light, the wearing state of the wearable device can be accurately distinguished by determining the fluctuation ranges of the four light intensity ratios.

It should be noted that, when selecting a type of the light source, it is better to select and combine a light source with different periodic fluctuations in the intensity of the reflected light after being reflected by the human body. For example, if only the red light and the infrared light are selected as a light source combination, since both reflected red light and reflected infrared light can reflect change characteristics of deeper subcutaneous tissues, the reflected red light and reflected infrared light are similar in light intensity and change period, which leads to a small calculated fluctuation range of the light intensity ratio, making it difficult to distinguish whether a subject is the human body or a stationary object. Therefore, it is better not to select these two light sources separately.

In a second aspect, an embodiment of the present disclosure provides a wearing state detection device for detecting a wearing state of a wearable device.

Figure 9:
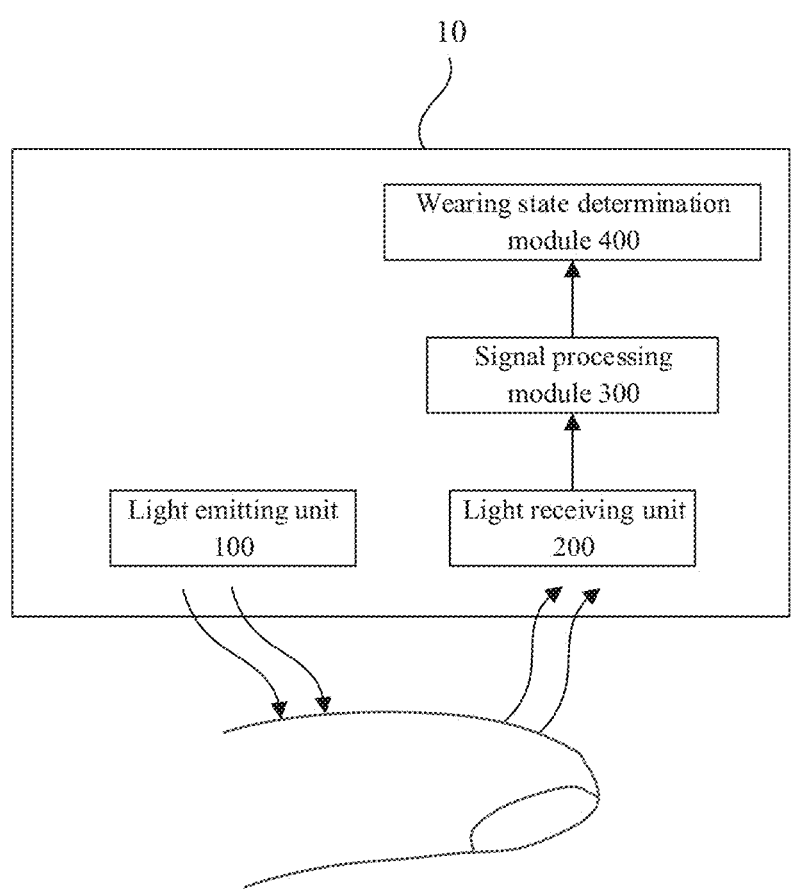
FIG. 9 is a structural diagram of a wearing state detection device according to an embodiment of the present disclosure.

As shown in FIG. 9, a structural diagram of a wearing state detection device according to an embodiment of the present disclosure is shown. The wearing state detecting device 10 includes a light emitting unit 100, a light receiving unit 200, a signal processing module 300, and a wearing state determination module 400.

The light emitting unit 100 can be a light emitting element such as a LED, and can emit light of at least two different wavelengths to a subject in a time division manner. The light receiving unit 200 can be a photosensitive element such as a PD, and can receive reflected light corresponding to light of each of the wavelengths after being reflected by the subject.

It should be noted that the type and number of the light sources emitted by the light emitting unit can be selected according to actual application scenarios or target requirements, and there are at least two types of light sources. When selecting the types of light sources, it is better to select a light source with different periodic fluctuations in the intensity of the reflected light after being reflected by the human body, such as green light and red light; or green light and infrared light; or green light, red light and infrared light. The light emitting unit can also be a light emitting element formed by packaging a plurality of different light sources together. In addition, the number of the light receiving units may be one or multiple. The light emitting unit and the light receiving unit can be independent devices in the wearable device or can be integrated together.

The signal processing module 300 can obtain intensity of reflected light corresponding to the light of the at least two different wavelengths respectively, and calculate a fluctuation range of a light intensity ratio.

If there are a plurality of light receiving units in the wearing state detection device, the light intensity ratio is a ratio between intensity of the reflected light corresponding to the light of the at least two different wavelengths received by a same light receiving unit.

When the fluctuation range of the light intensity ratio is greater than or equal to a first threshold, the wearing state determination module 400 can determine that the wearable device is in a wearing state; and when the fluctuation range of the light intensity ratio is smaller than the first threshold, the wearing state determination module 400 can determine that the wearable device is in a non-wearing state.

If it is determined that the wearable device is in a wearing state, functions such as detection of physiological parameters (such as heart rate and blood oxygen) can be started; and if it is determined that the wearable device is in a non-wearing state, it can be set to remind the user to wear the wearable device or wear the wearable device correctly, so as to obtain accurate and effective physiological parameter detection results.

The wearing state detection device according to the embodiments of the present disclosure can accurately distinguish whether the light emitting unit and the light receiving unit faces a human body or faces a relatively stationary object under a fluorescent lamp, thereby improving a rate of correctly response to the non-wearing state of the wearable device and accuracy of a wearing state detection result.

As a possible implementation, the signal processing module 300 can also acquire electrical signals output by the light receiving unit 200 after receiving the reflected light corresponding to the light of the at least two different wavelengths respectively to obtain raw data of intensity of the reflected light; acquire an electrical signal output by the light receiving unit 200 after receiving ambient light to obtain raw data of intensity of the ambient light before and/or after the light emitting unit 100 emits light of at least two different wavelengths to a subject in a time division manner; eliminate ambient light component contained in the raw data of intensity of the reflected light by using the raw data of intensity of the ambient light; and calculate the intensity of the reflected light corresponding to the light of the at least two different wavelengths respectively according to the raw data of intensity of the reflected light with the ambient light component being eliminated.

With the ambient light component contained in the raw data of intensity of the reflected light being eliminated, it is facilitated to more accurately calculating the intensity of the reflected light corresponding to the light of the at least two different wavelengths respectively, so as to more accurately calculate the light intensity ratio and further improve the accuracy of the wearing state detection result.

As a possible implementation, when the fluctuation range of the light intensity ratio is greater than or equal to the first threshold, the wearing state determination module 400 can further determine whether the fluctuation range of the light intensity ratio is smaller than a second threshold, which is greater than the first threshold. When the fluctuation range of the light intensity ratio is smaller than the second threshold, the wearing state determination module 400 can determine that the wearable device is in a well wearing state; and when the fluctuation range of the light intensity ratio is greater than or equal to the second threshold, the wearing state determination module 400 can determine that the wearable device is in a bad wearing state.

If it is determined that the wearable device is in a well wearing state, it can be set to start functions such as detection of physiological parameters (such as heart rate and blood oxygen); and if it is determined that the wearable device is in a bad wearing state, it can be set to send a prompt message to remind the user to wear the wearable device more tightly or stably, so as to obtain a more accurate wearing state detection result.

The first threshold and the second threshold can be determined by acquiring fluctuation ranges of the light intensity ratio of the wearable device in various wearing states in advance. For example, machine learning can be used to analyze and process the acquired fluctuation ranges of the light intensity ratio in advance, so as to determine initial values of the first threshold and the second threshold which can adapt to a basic application. By continuously acquiring relevant data of the fluctuation ranges of the light intensity ratio generated in the subject's subsequent use of the wearable device, values of the first threshold and the second threshold can be iteratively updated, so as to further improve individual adaptability and the accuracy of the wearing state detection result.

In a third aspect, an embodiment of the present disclosure provides a wearable device, which includes the wearing state detection device according to any embodiment of FIG. 9.

The wearable device according to this embodiment of the present disclosure can implement the above-described method embodiments with the similar implementation principle and technical effect, which will not be repeatedly described herein.

Finally, it should be noted that the above embodiments are intended to only illustrate the technical scheme of the present disclosure, but not to limit thereto; although the present disclosure has been described in detail with reference to the foregoing embodiments, it should be understood for those of ordinary skilled in the art that the technical solutions described in the foregoing embodiments can still be modified or some or all of the technical features can be replaced equivalently; and these modifications or substitutions do not cause essence of the corresponding technical solutions to deviate from a scope of the technical solutions of each embodiment of the present disclosure.

What is claimed is:

1. A wearing state detection method for detecting a wearing state of a wearable device, wherein the wearable device comprises a light emitting unit and a light receiving unit, and the wearing state detection method comprises:
    emitting, by the light emitting unit, light of at least two different wavelengths to a subject in a time division manner;
    receiving, by the light receiving unit, reflected light corresponding to light of each of the at least two different wavelengths after being reflected by the subject;
    obtaining intensity of reflected light corresponding to the light of each of the at least two different wavelengths, respectively;
    calculating a fluctuation range of a light intensity ratio, the light intensity ratio being a ratio between intensity of the reflected light corresponding to the light of the at least two different wavelengths received by a same light receiving unit; and
    determining that the wearable device is in a wearing state when the fluctuation range of the light intensity ratio is greater than or equal to a first threshold,
    wherein absorption and reflectivity of the light of the at least two different wavelengths by a human body are different,
    wherein said obtaining the intensity of the reflected light corresponding to the light of the at least two different wavelengths further comprises:
    acquiring an electrical signal output by the light receiving unit after receiving the reflected light corresponding to the light of each of the at least two different wavelengths, respectively, to obtain raw data of intensity of the reflected light;
    acquiring an electrical signal output by the light receiving unit after receiving ambient light to obtain raw data of intensity of the ambient light before and/or after the light emitting unit emits the light of the at least two different wavelengths to the subject in a time division manner:
    eliminating ambient light component contained in the raw data of intensity of the reflected light by using the raw data of intensity of the ambient light; and
    calculating the intensity of the reflected light corresponding to the light of each of the at least two different wavelengths respectively based on the raw data of intensity of the reflected light with the ambient light component being eliminated.

2. The wearing state detection method according to claim 1, further comprising:
    determining that the wearable device is in a non-wearing state when the fluctuation range of the light intensity ratio is smaller than the first threshold.

3. The wearing state detection method according to claim 1, further comprising, when the fluctuation range of the light intensity ratio is greater than or equal to the first threshold:
    determining that the wearable device is in a well wearing state when the fluctuation range of the light intensity ratio is smaller than a second threshold, the second threshold being greater than the first threshold.

4. The wearing state detection method according to claim 3, further comprising:
    determining that the wearable device is in a bad wearing state when the fluctuation range of the light intensity ratio is greater than or equal to the second threshold.

5. The wearing state detection method according to claim 1, wherein the light of the at least two different wavelengths comprises green light and red light;
or green light and infrared light; or green light, red light and infrared light.

6. A wearing state detection device for detecting a wearing state of a wearable device, wherein the wearing state detection device comprises:
a light emitting unit configured to emit light of at least two different wavelengths to a subject in a time division manner;
a light receiving unit configured to receive reflected light corresponding to light of each of the at least two different wavelengths after being reflected by the subject;
a signal processing module configured to obtain intensity of reflected light corresponding to the light of each of the at least two different wavelengths respectively, and calculating a fluctuation range of a light intensity ratio, the light intensity ratio being a ratio between intensity of the reflected light corresponding to the light of the at least two different wavelengths received by a same light receiving unit; and
a wearing state determination module configured to determine that the wearable device is in a wearing state when the fluctuation range of the light intensity ratio is greater than or equal to a first threshold,
wherein absorption and reflectivity of the light of the at least two different wavelengths by a human body are different,
wherein the signal processing module is further configured to:
acquire an electrical signal output by the light receiving unit after receiving the reflected light corresponding to the light of each of the at least two different wavelengths respectively, to obtain raw data of intensity of the reflected light;
acquire an electrical signal output by the light receiving unit after receiving ambient light to obtain raw data of intensity of the ambient light before and/or after the light emitting unit emits the light of the at least two different wavelengths to the subject in a time division manner;
eliminate ambient light component contained in the raw data of intensity of the reflected light by using the raw data of intensity of the ambient light; and
calculate the intensity of the reflected light corresponding to the light of each of the at least two different wavelengths respectively based on the raw data of intensity of the reflected light with the ambient light component being eliminated.

7. The wearing state detection device according to claim 6, wherein the wearing state determination module is further configured to:
determine that the wearable device is in a non-wearing state when the fluctuation range of the light intensity ratio is smaller than the first threshold.

8. The wearing state detection device according to claim 6, wherein the wearing state determination module is further configured to, when the fluctuation range of the light intensity ratio is greater than or equal to the first threshold:
determine that the wearable device is in a well wearing state when the fluctuation range of the light intensity ratio is smaller than a second threshold, the second threshold being greater than the first threshold.

9. The wearing state detection device according to claim 8, wherein the wearing state determination module is further configured to:
determine that the wearable device is in a bad wearing state when the fluctuation range of the light intensity ratio is greater than or equal to the second threshold.

10. The wearing state detection device according to any of claim 6, wherein the light of the at least two different wavelengths comprises green light and red light; or green light and infrared light; or green light, red light and infrared light.

11. A wearable device comprising:
a light emitting unit configured to emit light of at least two different wavelengths to a subject in a time division manner;
a light receiving unit configured to receive reflected light corresponding to light of each of the at least two different wavelengths after being reflected by the subject;
a signal processing module configured to obtain intensity of reflected light corresponding to the light of each of the at least two different wavelengths respectively, and calculating a fluctuation range of a light intensity ratio, the light intensity ratio being a ratio between intensity of the reflected light corresponding to the light of the at least two different wavelengths received by a same light receiving unit; and
a wearing state determination module configured to determine that the wearable device is in a wearing state when the fluctuation range of the light intensity ratio is greater than or equal to a first threshold,
wherein absorption and reflectivity of the light of the at least two different wavelengths by a human body are different,
wherein the signal processing module is further configured to:
acquire an electrical signal output by the light receiving unit after receiving the reflected light corresponding to the light of each of the at least two different wavelengths respectively, to obtain raw data of intensity of the reflected light;
acquire an electrical signal output by the light receiving unit after receiving ambient light to obtain raw data of intensity of the ambient light before and/or after the light emitting unit emits the light of the at least two different wavelengths to the subject in a time division manner;
eliminate ambient light component contained in the raw data of intensity of the reflected light by using the raw data of intensity of the ambient light; and
calculate the intensity of the reflected light corresponding to the light of each of the at least two different wavelengths respectively based on the raw data of intensity of the reflected light with the ambient light component being eliminated.

12. The wearable device according to claim 11, wherein the wearing state determination module is further configured to:
determine that the wearable device is in a non-wearing state when the fluctuation range of the light intensity ratio is smaller than the first threshold.

13. The wearable device according to claim 11, wherein the wearing state determination module is further configured to, when the fluctuation range of the light intensity ratio is greater than or equal to the first threshold:
determine that the wearable device is in a well wearing state when the fluctuation range of the light intensity ratio is smaller than a second threshold, the second threshold being greater than the first threshold.

14. The wearable device according to claim 13, wherein the wearing state determination module is further configured to:
   determine that the wearable device is in a bad wearing state when the fluctuation range of the light intensity ratio is greater than or equal to the second threshold.

15. The wearable device according to claim 11, wherein the light of the at least two different wavelengths comprises green light and red light; or green light and infrared light; or green light, red light and infrared light.

16. The wearable device according to claim 12, when the wearable device is in the non-wearing state, a first prompt message is output to remind a user to wear the wearable device or wear the wearable device correctly.

17. The wearable device according to claim 14, when the wearable device is in the bad wearing state, a second prompt message can be output to remind a user to wear the wearable device tightly or stably.

\* \* \* \* \*